United States Patent [19]

Yu et al.

[11] Patent Number: 5,877,212

[45] Date of Patent: Mar. 2, 1999

[54] MOLECULAR COMPLEX AND CONTROL-RELEASE OF ALPHA HYDROXYACIDS

[76] Inventors: Ruey J. Yu, 4 Lindenwold Ave., Ambler, Pa. 19002; Eugene J. Van Scott, 3 Hidden La., Abington, Pa. 19001

[21] Appl. No.: 842,603

[22] Filed: Apr. 16, 1997

[51] Int. Cl.$^6$ .......................... A61K 31/19; A61K 31/70; A61K 31/715; A61K 31/56

[52] U.S. Cl. .............. 514/557; 514/31; 514/54; 514/178; 514/256; 514/383; 514/419; 514/458; 514/460; 514/562; 514/566; 514/574

[58] Field of Search ..................... 514/557, 574, 514/566, 54, 31, 256, 383, 458, 460, 178, 562, 419

[56] References Cited

U.S. PATENT DOCUMENTS

| | | | |
|---|---|---|---|
| 3,879,537 | 4/1975 | Van Scott et al. | 514/460 |
| 3,920,835 | 11/1975 | Van Scott et al. | 514/460 |
| 4,363,815 | 12/1982 | Yu et al. | 514/263 |
| 5,091,171 | 2/1992 | Yu et al. | 424/642 |
| 5,425,938 | 6/1995 | Znaiden et al. | 424/78.02 |

OTHER PUBLICATIONS

Chemical Abstracts (126: 268321) Marianos et al. 1997.

*Primary Examiner*—Kevin E. Weddington
*Attorney, Agent, or Firm*—Foley & Lardner

[57] ABSTRACT

Compositions comprising an alpha hydroxyacid or related acid and organic complexing agent having a molecular weight ranging preferably between about 100 and about 600 can form a control-release molecular complex. Such complexing agent preferably possesses one or more amino group in addition to other groups with unshared electrons such as hydroxyl, carbonyl, amido, ester and alkoxyl groups in the same molecule. Such functional groups are capable of forming multiple intermolecular hydrogen bonds with the hydroxyl groups of a free alpha hydroxyacid or related acid. The complexing agents include amino acid esters, non-amphoteric amino acid amides, aminosaccharides, aminoalditols and aminocyclitols.

54 Claims, No Drawings

MOLECULAR COMPLEX AND CONTROL-RELEASE OF ALPHA HYDROXYACIDS

FIELD OF THE INVENTION

This application relates to topical compositions containing a controlled-release molecular complex formed between an alpha hydroxyacid or related acid and an organic complexing compound. The compositions are topically beneficial for various cosmetic and dermatologic indications.

In an embodiment of the invention, an alpha hydroxyacid or related acid can form a control-release molecular complex with an organic complexing agent having an amino group and at least one of other groups which can form multiple hydrogen bonds with a free alpha hydroxyacid or related acid. Due to control-release characteristic of the molecular complex, compositions containing such complex is topically effective for cosmetic and dermatologic indications of skin, nail and hair without skin irritation.

BACKGROUND OF THE INVENTION

In our prior U.S. Pat. No. 3,879,537 entitled "Treatment of Ichthyosiform Dermatoses" we described and claimed the use of certain alpha hydroxyacids, alpha ketoacids and related compounds for topical treatment of fish-scale like ichthyotic conditions in humans. In our U.S. Pat. No. 3,920,835 entitled "Treatment of Disturbed Keratinization" we described and claimed the use of these alpha hydroxyacids, alpha ketoacids and their derivatives for topical treatment of dandruff, acne, and palmar and plantar hyperkeratosis.

In our prior U.S. Pat. No. 4,105,783 entitled "Treatment of Dry Skin" we described and claimed the use of non-irritating compositions containing reaction products formed between an alpha hydroxyacid or alpha ketoacid and ammonium hydroxide or an organic primary, secondary or tertiary alkyl amine or the like having from 1 to 8 carbon atoms, for topical treatment of dry skin. In our recent U.S. Pat. No. 4,246,261 entitled "Additives Enhancing Topical Corticosteroid Action" we described and claimed that alpha hydroxyacids, alpha ketoacids and their derivatives could greatly enhance the therapeutic efficacy of corticosteroids in topical treatment of psoriasis, eczema, seborrheic dermatitis and other inflammatory skin conditions.

In our U.S. Pat. No. 4,363,815 entitled "Alpha Hydroxyacids, Alpha Ketoacids and Their Use in Treating Skin Conditions" we described and claimed that alpha hydroxyacids and alpha ketoacids related to or originating from amino acids, whether or not found in proteins, were effective in topical treatment of skin disorders associated with disturbed keratinization or inflammation. These skin disorders include dry skin, ichthyosis, palmar and plantar hyperkeratosis, dandruff, Darier's disease, lichen simplex chronicus, keratoses, acne, psoriasis, eczema, pruritus, warts and herpes.

In our recent U.S. patent application Ser. No. 945,680 filed Dec. 23, 1986 now abandoned and entitled "Additives Enhancing Topical Actions of Therapeutic Agents", we described among other things that incorporation of an alpha hydroxyacid or related compound can substantially enhance therapeutic actions of cosmetic and pharmaceutical agents. We also described methods of treating wrinkles and skin changes associated with aging using an alpha hydroxyacid or related compound.

In our more recent U.S. patent application Ser. No. 393,749 filed Aug. 15, 1989 and entitled "Amphoteric Compositions and Polymeric Forms of Alpha Hydroxyacids, and Their Therapeutic Use", now U.S. Pat. No. 5,091,171, we described among other things compositions containing an amphoteric complex formed between an alpha hydroxyacid or related compound and an amphoteric or pseudoamphoteric agent are therapeutically effective for topical treatment of various cosmetic conditions and dermatologic indications.

In our most recent U.S patent application Ser. No. 683,437 filed Apr. 10, 1991 and entitled "Compositions Comprising 2-Hydroxycarboxylic Acid and Related Compounds, and Methods for Alleviating Signs of Dermatologic Aging", now abandoned we described among other things that compositions containing an alpha hydroxyacid or related compound are therapeutically effective for topical treatment of dermatological signs of aging. The signs of aging include changes or damage to skin, nail and hair associated with intrinsic aging, as well as changes or damage caused by extrinsic factors such as sunlight, radiation, air pollution, wind, cold, heat, dampness, chemicals, smoke and cigarette smoking.

In recent U.S. Pat. No. 5,425,938 entitled "Polyamino Salts of Alpha-Hydroxyacids, Alpha-Ketoacids and Related Compounds" it is disclosed that such polyamino salts might be used in cosmetic compositions. The claimed amino polymers have optimal molecular weights of from 10,000 to 800,000. However, according to Jackson S. M., Elias P. M.: SKIN AS AN ORGAN OF PROTECTION cited in Fitzpatrick T. B., Eisen A. Z., Wolff K., Freedberg I. M., Austen K. F. (ed.): DERMATOLOGY IN GENERAL MEDICINE, 4th edition, McGraw-Hill, Inc., New York; 1993: Chapter 16, 241–253, experiments have shown that even non-polar polymers with molecular weight of above 800–1000 decrease dramatically in penetration through the stratum corneum of the skin. Therefore, such amino polymers cannot readily penetrate the stratum corneum of human skin due to their high molecular weight and polar nature of the polyamino salt.

Each of the foregoing patents and applications is expressly incorporated herein by reference in their entireties.

It has been established through scientific and clinical studies that alpha hydroxyacids and related acids are therapeutically effective for topical treatment of various cosmetic and dermatologic indications associated with disturbed keratinization and skin changes associated with aging. However, the compositions containing these acids may irritate human skin on repeated topical applications, due to lower pH of the formulations and uncontrolled release and penetration of the acids into stratum corneum of the skin. We have found, for example, that a product containing 12% lactic acid with pH 4.8 can still irritate sensitive skin or atopic skin if the composition is not formulated under controlled-release basis.

SUMMARY OF THE INVENTION

We have now discovered that an alpha hydroxyacid or related acid can form a control-release molecular complex with an organic complexing agent having a molecular weight ranging preferably between about 100 and about 600. Such complexing agent preferably possesses one or more amino group in addition to other groups with unshared electrons such as hydroxyl, carbonyl, amido, ester and alkoxyl groups in the same molecule. Such functional groups are capable of forming multiple intermolecular hydrogen bonds with the hydroxyl groups of a free alpha hydroxyacid or related acid. The complexing agents include amino acid esters, non-amphoteric amino acid amides, aminosaccharides, aminoalditols and aminocyclitols.

A topical composition containing such molecular complex has two advantages, namely (a) higher pH and (b) control-release of an active ingredient into the skin nail or hair. We have found that such composition is topically effective for various cosmetic and dermatologic indications without skin irritations.

The cosmetic and dermatologic indications are characterized as disturbed keratinization, defective syntheses of dermal components, and skin changes associated with aging; and those indications which include dry skin; xerosis; ichthyosis; palmar and plantar hyperkeratoses; rough skin; dandruff; Darier's disease; lichen simplex chronicus; keratoses; acne; pseudofolliculitis barbae; eczema; psoriasis; pruritus; warts; herpes; age spots; lentigines; melasmas; blemished skin; hyperkeratoses; hyperpigmented skin; abnormal or diminished syntheses of collagen, glycosaminoglycans, proteoglycans and elastin as well as diminished levels of such compounds in the dermis; stretch marks; skin lines; fine lines; wrinkles; thinning of skin; loss of skin elasticity and recoilability; older-looking skin; yellowing skin; and other topical conditions and indications. The topical composition containing the molecular complex has also been found to promote skin smoothing, skin softening and younger looking skin.

DESCRIPTION OF THE PREFERRED EMBODIMENTS (I) Physicochemical Properties

In order to comprehend the molecular complex formed between an alpha hydroxyacid or related acid and a complexing agent, it is helpful to discuss acidity and pKa of the acid. The relative acid strength of an acid is measured by its proton dissociation in aqueous solution and is expressed as the pKa of the acid. For example, when glycolic acid (HA) is dissolved in water some molecules will dissociate into glycolate anion ($A^-$) and hydrogen cation ($H^+$). When an equilibrium is reached for example at room temperature (25° C.), the equilibrium constant Ka is defined as $[H^+][A^-]/[HA]$ in which [HA] is concentration of the undissociated free glycolic acid in solution. The pKa and pH are negative logarithm of Ka and [$H^+$] respectively. The pKa values of some alpha hydroxyacids and related acids are shown in Table 1. Some alpha hydroxyacids have two or three carboxyl groups such as tartaric acid and citric acid, and pKa of the second and third carboxyl groups are denoted as $pK_2$ and $pK_3$ respectively.

Since the pKa is a negative logarithm of the dissociation constant, the difference of 1 unit in pKa represents a tenfold difference in the acid strength. Therefore, an alpha hydroxyacid acid is a stronger acid if its pKa number is lower. For example, mandelic acid (pKa 3.41) is a stronger acid than glycolic acid (pKa 3.83). The pKa value of an alpha hydroxyacid determines not only the acid potency but also the amount of free acid which exists at a particular pH of the formulation. For example, at pH 3.83, glycolic acid 10% formulation at room temperature contains glycolic acid 5% as a free acid and 5% as glycolate anion. At pH 3.2, glycolic acid 10% formulation contains glycolic acid 8% as a free acid and 2% as glycolate anion. In the same manner, at pH 3.86 L-lactic acid (pKa 3.86) 10% formulation contains lactic acid 5% as a free acid and 5% as lactate anion. At pH 4.5, lactic acid 10% formulation contains lactic acid 2% as a free acid and 8% as lactate anion.

In general, the free acid is substantially more bioavailable for the first phase of permeation into the intact skin, but the anion is less bioavailable.

TABLE 1 pKa of Alpha Hydroxyacids and Related Acids at 25° C.

| | $pK_1$ (pKa) | $pK_2$ | $pK_3$ |
|---|---|---|---|
| L-Ascorbic acid | 4.17 | | |
| Atrolactic acid | 3.53 | | |
| Benzilic acid | 3.09 | | |
| 3-Chlorolactic acid | 3.12 | | |
| Citric acid | 3.13 | 4.76 | 6.40 |
| Glucaric acid | 5.00 | | |
| D-Gluconic acid | 3.86 | | |
| DL-Glyceric acid | 3.64 | | |
| Glycolic acid | 3.83 | | |
| 2-Hydroxybutanoic acid | 3.65 | | |
| L-3-Hydroxybutanoic acid | 4.41 | | |
| L-Lactic acid | 3.86 | | |
| Malic acid | 3.46 | 5.10 | |
| Mandelic acid | 3.41 | | |
| Methyllactic acid | 3.72 | | |
| Pyruvic acid | 2.49 | | |
| D-Tartaric acid | 3.04 | 4.37 | |
| Tartronic acid | 2.37 | 4.74 | |
| Tropic acid | 3.53 | | |

(II) Molecular Complex

In the instant invention, an alpha hydroxyacid or related acid reacts with a complexing agent which has at least one amino group in addition to one of other groups such as hydroxyl, carbonyl, amido, ester or alkoxyl group in the same molecule. The molar ratio of the alpha hydroxyacid to the complexing agent may range from 0.5 to 100 with preferred ratio of 1 to 20. Under such conditions, the molecular complex consists primarily of the following molecular species, (a) undissociated alpha hydroxyacid, (b) alpha hydroxyacid anion and (c) complexing agent cation.

The hydroxyl groups at the alpha position and at the carboxyl end of the undissociated alpha hydroxyacid can form hydrogen bonds with the hydroxyl, carbonyl, amido or alkoxyl group of the complexing agent cation. In general, a hydrogen bond is formed between a hydrogen atom of a hydroxyl group and an oxygen or nitrogen atom with a pair of unshared electrons in a hydroxyl, carboxyl, amido, ester or alkoxyl group. The alpha hydroxyacid anion and the complexing agent cation are bound together in ionic linkage as carboxylic and ammonium bond.

The undissociated alpha hydroxyacid is immediately bioavailable for permeation into the skin, but is under the control-release mechanism created by the hydrogen bonds. The ionic species of alpha hydroxyacid anion and complexing agent cation are bound by an ionic bond and are less bioavailable for permeation into the intact skin. Under such conditions hydrogen bonds are strong enough to control and release the undissociated alpha hydroxyacid into the stratum corneum, but are weak enough to release more acid at a steady rate. Thus, alpha hydroxyacid or related acid is continuously bioavailable and control-released at an optimal rate without irritation to the skin.

We have found that compositions containing the above molecular complex are therapeutically beneficial for topical management and treatment of various cosmetic and dermatologic indications. For example, when glycolic acid 25 g (0.33 mole) is reacted with glucosamine base 5.4 g (0.03 mole) in water 26.6 ml, propylene glycol 20 ml and ethanol 23 ml, the pH is approximately 2.6. Under such conditions, the molecular complex consists of the following species: undissociated free glycolic acid 0.30 mole, glycolate anion 0.03 mole and glucosammonium cation 0.03 mole. The hydroxyl groups at the alpha position and at the carboxyl end of undissociated free glycolic acid can form multiple hydrogen bonds with four hydroxyl groups of glucosammonium cation.

When a composition containing the above molecular complex is topically applied to the skin, the glycolate anion 0.03 mole and the glucosammonium cation 0.03 mole are less bioavailable in the first phase of permeation and therefore will remain at the surface of the stratum corneum. The undissociated glycolic acid 0.30 mole is bioavailable for permeation, but is under the control-release mechanism created by the hydrogen bonds. Under such conditions hydrogen bonds are strong enough to hold and control the rate of permeation of free glycolic acid into the stratum corneum, but are weak enough to release more glycolic acid after the penetration of some glycolic acid into the skin. Thus, glycolic acid is constantly bioavailable and control-released at an optimal rate without irritation to the skin.

(III) Complexing Agents

Complexing agents which can form a molecular complex with an alpha hydroxyacid or related acid comprise organic amino compounds in free base form having one or more other functional groups with unshared electrons such as hydroxyl, carbonyl, amido, ester and alkoxyl groups. The amino group of the complexing agent forms an ionic bond with the carboxyl group of dissociated alpha hydroxyacid or related acid. The functional groups form hydrogen bonds with the hydroxyl groups of the undissociated alpha hydroxyacid or related acid. The molecular weight of the complexing agent may range from about 50 to about 900 (e.g., from 50 to 900) with preferred range of from about 100 to about 600 (e.g., from 100 to 600) so that the complexing agent may also slowly and steadily permeate into the stratum corneum of the skin.

The complexing agents include amino acid esters, non-amphoteric amino acid amides, aminosaccharides, aminoalditols and aminocyclitols. Many potentially useful complexing agents are commercially available but only as hydrochloride or other salt forms. Such salt forms can not form a molecular complex with an alpha hydroxyacid or related acid unless the complexing agent is converted to free base form. For example, a simple procedure has been developed to liberate the free base form by reacting the salt with an equimolar amount of 5N sodium hydroxide or potassium hydroxide solution at ice-water temperature. The complexing agent in free base form thus liberated may be used immediately for the formation of a molecular complex. Other acceptable procedures will be apparent to skilled artisans.

(A) Amino Acid Esters

These esters include alkyl, aralkyl and aryl esters of amino acids derived from naturally occurring proteins or from other sources such as microorganisms. Typical alkyl, aralkyl and aryl groups include methyl, ethyl, propyl, isopropyl, butyl, pentyl, octyl, lauryl, stearyl, benzyl and phenyl esters. Representative esters of amino acids and similar compounds include methyl, ethyl, propyl and benzyl esters of glycine, alanine, valine, leucine, isoleucine, serine, threonine, tyrosine, cysteine, methionine, aspartic acid, asparagine, glutamic acid, glutamine, arginine, lysine, histidine, phenylalanine, tryptophan, proline, β-alanine, β-aminoisobutanoic acid, homocysteine, homoserine, ornithine and citrulline.

As an illustration, when L-lactic acid (2 moles) reacts with glycine ethyl ester (1 mole), the molecular complex thus formed with an approximate pH of 3.86 may contain undissociated lactic acid (1 mole), lactate anion (1 mole) and glycine ethyl ester cation (1 mole). The hydrogen atom of the hydroxyl groups at the alpha position and at the carboxyl end of the undissociated lactic acid will form hydrogen bonds with the oxygen atoms of the carbonyl and ethoxyl groups of the glycine ester cation as well as with the oxygen atom of the hydroxyl group at the alpha position of dissociated lactate anion. The undissociated lactic acid (1 mole) is bioavailable for permeation into the skin but is under the control-release mechanism by the hydrogen bonds.

(B) Amino Acid Amides

These complexing agents include the amide form of amino acids without amphoteric properties, such as glycinamide and glutaminamide. Two hydrogen atoms of the amide group may be unsubstituted or substituted by alkyl, aralkyl or aryl radicals, for example in glycinmethylamide and glycindimethylamide. Representative amino acid amides include glycinamide, alaninamide, valinamide, leucinamide, isoleucinamide, serinamide, threoninamide, tyrosinamide, cysteinamide, methioninamide, asparaginamide, glutaminamide, argininamide, lysinamide, histidinamide, phenylalaninamide, tryptophanamide, prolinamide, β-alaninamide, β-aminoisobutanoic amide, homocysteinamide, homoserinamide, ornithinamide and citrullinamide.

As an illustration, when gluconic acid (2 moles) reacts with serinamide (1 mole) a molecular complex is formed with an approximate pH of 3.86. The complex may consist of undissociated gluconic acid (1 mole), gluconate anion (1 mole) and serinamide cation (1 mole). Hydrogen bonds may form between the hydroxyl groups of undissociated gluconic acid and the hydroxyl group as well as amido group of serinamide. Other hydrogen bonds may also form between the hydroxyl groups of undissociated gluconic acid and gluconate anion.

(C) Aminosaccharides

These complex agents are amino derivatives of monosaccharides and oligosaccharides such as glucosamine, mannosamine, galactosamine and sucrosamine. Aminosaccharides may contain more than one amino group but preferred number is one amino group per molecule.

Representative aminomonosaccharides include: erythrosylamines, erythrosamines, threosylamines, threosamines, ribosylamines, ribosamines, arabinosylamines, arabinosamines, xylosylamines, xylosamines, lyxosylamines, lyxosamines, allosylamines, allosamines, altrosylamines, altrosamines, glucosylamines, glucosamines, mannosylamines, mannosamines, gulosylamines, gulosamines, idosylamines, idosamines, galactosylamines, galactosamines, talosylamines, talosamines, glucoheptosylamines, glucoheptosamines, galactoheptosylamines, galactoheptosamines, mannoheptosylamines, mannoheptosamines, octosylamines, octosamines, nonosylamines, nonosamines, tetrulosamines, erythrulosamines, pentulosamines, ribulosamines, arabulosamines, xylulosamines, lyxulosamines, hexulosamines, fructosamines, sorbosamines, tagatosamines. Representative aminooligosaccharides are listed below. Sucrosamines, lactosylamines, lactosamines, trehalosamines, maltosylamines, maltosamines, cellobiosylamines, cellobiosamines, isomaltosylamines, isomaltosamines, gentiobiosylamines, gentiobiosamines, chitobiose and chitobiosylamines.

As an illustration, when glycolic acid (2 moles) reacts with glucosamine (1 mole) a molecular complex is formed with an approximate pH of 3.83. The complex may consist of undissociated glycolic acid (1 mole), glycolate anion (1 mole) and glucosamine cation (1 mole). Hydrogen bonds may form between the hydroxyl group of undissociated glycolic acid and the hydroxyl groups of glucosamine cation.

(D) Aminoalditols

These complexing agents are reduced forms of aminosaccharides in which the aldehyde or keto group has been reduced to an hydroxyl group. Representative aminoalditols include: aminoerythritols, aminothreitols, threamine, aminoribitols, ribamine, aminoarabinitols, arabinamine, aminoxylitols, xylamine, aminolyxitols, lyxamine, aminoallitols, allamine, aminoaltritols, altramine, aminoglucitols, glucamine, aminomannitols, mannamine, aminogulitols, gulamine, aminoiditols, idamine, aminogalactitols, galactamine, aminotalitols, talamine, aminoalloheptitols and alloheptamine.

As an illustration, when methyllactic acid (2 moles) reacts with glucamine (1 mole), a molecular complex is formed with an approximate pH of 3.72. The complex may consist of undissociated methyllactic acid (1 mole), methyllactate anion (1 mole) and glucamine cation (1 mole). Hydrogen bonds may form between the hydroxyl groups of undissociated methyllactic acid and the hydroxyl groups of glucamine.

(E) Aminocyclitols

These complexing agents are amino derivatives of cyclitols which are hydroxycycloalkanes usually having two or more hydroxyl groups attached to carbon atoms in the ring. Representative aminocyclitols include: cis-Aminoinositol, epi-aminoinositols, neo-aminoinositols, myo-aminoinositol, muco-aminoinositols, scyllo-aminoinositols, chiro-aminoinositols, validamine, valienamine and aminopinitols.

As an illustration, when citric acid (2 moles) reacts with aminoinositol (1 mole), a molecular complex is formed with an approximate pH of 3.13. The complex may consist of undissociated citric acid (1 mole), citrate anion (1 mole) and aminoinositol cation (1 mole). Hydrogen bonds may form between the hydroxyl group of undissociated citric acid and the hydroxyl groups of aminoinositol.

(IV) Effects on Epidermal and Dermal Components

Glycosaminoglycans, known as GAGs, mucopolysaccharides or ground substances, are important macromolecules along with collagen and elastic fibers in the dermis, and also play an important role in the epidermis as an intercellular cementing material between keratinocytes. In human skin, major GAGs are hyaluronates, chondroitin sulfate, keratan sulfates, dermatan sulfate, heparan and heparin sulfate. Many of these GAGs are covalently linked to proteins and form proteoglycans having high molecular weights ranging from 230,000 to 2,500,000. Physiological functions of GAGs and proteoglycans in human skin include binding abundant water to form gelatinous materials and playing an important role in wound healing and repair of skin changes associated with aging.

Due to their high molecular weights, proteoglycans and GAGs are unable to penetrate stratum corneum of intact human skin. Since proteoglycans and GAGs are formed from amino acids, aminosaccharides and other complexing agents of the instant invention, it is expected that topical administration of these agents alone without alpha hydroxyacids may also stimulate and activate biosyntheses of these macromolecule components. In this regard, we have found that the molecular complex or the complexing agent of the instant invention on topical application to the skin can activate biosyntheses of proteoglycans and GAGs as shown by the increased thickness of the skin which was measured clinically and histologically.

(V) Alpha Hydroxyacids and Related Acids

In accordance with the instant invention, the alpha hydroxyacid or related acid which forms a molecular complex with a complexing agent may be discussed in three groups, (A) alpha hydroxyacids, (B) related acids, and (C) partial salt and lactone form. Each of these groups is discussed below, and in the above-cited patents and applications, which have been incorporated herein by reference.

(A) Alpha Hydroxyacids

The alpha hydroxyacid is an organic carboxylic acid in which one hydroxyl group is attached to the alpha carbon of the acids. The generic structure of such alpha hydroxyacids may be represented as follows:

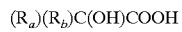

$(R_a)(R_b)C(OH)COOH$ where $R_a$ and $R_b$ are H, F, Cl, Br, I, alkyl, aralkyl or aryl group of saturated or unsaturated, isomeric or non-isomeric, straight or branched chain or cyclic form, having 1 to 25 carbon atoms, and in addition $R_a$ and $R_b$ may carry OH, CHO, COOH and alkoxyl group having 1 to 9 carbon atoms. The hydrogen atom attached to the carbon atom may be substituted by F, Cl, Br, I, or lower alkyl, aralkyl, aryl or alkoxyl group having 1 to 9 carbon atoms. The alpha hydroxyacids may be present as a free acid or lactone form, or in a partial salt form with an organic base or an inorganic alkali. The alpha hydroxyacids may exist as stereoisomers such as D, L, DL and meso forms.

When Ra and Rb are alkyl, they independently can be within any of the groups of C1–C5, C6–C10, C11–C15, C16–C20, C21–C25 and C26–C29. Compounds within the invention thus include all of the possible combinations of Ra and Rb. Included within the foregoing is a subgenus of compounds having Ra and Rb independently selected from C1–C12.

Typical alkyl, aralkyl, aryl and alkoxyl groups for $R_a$ and $R_b$ include methyl, ethyl, propyl, propyl, isopropyl, butyl, pentyl, octyl, lauryl, stearyl, benzyl, phenyl, methoxyl, and ethoxyl. The alpha hydroxyacids of the first group may be subdivided into (1) alkyl alpha hydroxyacids, (2) aralkyl and aryl alpha hydroxyacids, (3) polyhydroxy alpha hydroxyacids, (4) polycarboxylic alpha hydroxyacids and (5) miscellaneous alpha hydroxyacids. The following are representative alpha hydroxyacids in each subgroup.

(1) Alkyl Alpha Hydroxyacids: 2-hydroxyethanoic acid (glycolic acid), 2-hydroxypropanoic acid (lactic acid), 2-methyl 2-hydroxypropanoic acid (methyllactic acid), 2-hydroxybutanoic acid, 2-hydroxypentanoic acid, 2-hydroxyhexanoic acid, 2-hydroxyheptanoic acid, 2-hydroxyoctanoic acid, 2-hydroxynonanoic acid, 2-hydroxydecanoic acid, 2-hydroxyundecanoic acid, 2-hydroxydodecanoic acid, 2-hydroxytetradecanoic acid, 2-hydroxyhexadecanoic acid, 2-hydroxyoctadecanoic acid, 2-hydroxyeicosanoic acid (alpha hydroxyarachidonic acid), 2-hydroxytetraeicosanoic acid (cerebronic acid), 2-hydroxytetraeicosenoic acid (alpha hydroxynervonic acid) and 2,4-dihydroxy-3,3-dimethylbutanoic acid (pantoic acid)

(2) Aralkyl And Aryl Alpha Hydroxyacids: 2-phenyl 2-hydroxyethanoic acid (mandelic acid); 2,2-diphenyl 2-hydroxyethanoic acid (benzilic acid), 3-phenyl 2-hydroxypropanoic acid (phenyllactic acid), 2-phenyl 2-methyl 2-hydroxyethanoic acid (atrolactic acid) and 4-hydroxymandelic acid.

(3) Polyhydroxy Alpha Hydroxyacids: 2,3-dihydroxypropanoic acid (glyceric acid); 2,3,4-trihydroxybutanoic acid (isomers; erythronic acid, threonic acid); 2,3,4,5-tetrahydroxypentanoic acid (isomers; ribonic acid, arabinoic acid, xylonic acid, lyxonic acid); 2,3,4,5,6-pentahydroxyhexanoic acid (isomers; allonic acid, altronic acid, gluconic acid, mannoic acid, gulonic acid, idonic acid, galactonic acid, talonic acid); 2,3,4,5,6,7- hexahydroxyheptanoic acid (isomers; glucoheptonic acid, galactoheptonic acid, mannoheptonic acid, etc.)

(4) Polycarboxylic Alpha Hydroxyacids: 2-hydroxypropane-1,3-dioic acid (tartronic acid); 2-hydroxybutane-1,4-dioic acid (malic acid); 2-hydroxy-2-methylbutane-1,4-dioic acid (citramalic acid); 2,3-dihydroxybutane-1,4-dioic acid (tartaric acid); 2,3,4-trihydroxypentane-1,5-dioic acid (isomers; ribaric acid, arabaric acid, xylaric acid, lyxaric acid); 2,3,4,5-tetrahydroxyhexane-1,6-dioic acid (isomers; glucaric acid, galactaric acid, mannaric acid, allaric acid, altraric acid, gularic acid, idaric acid, talaric acid); 2-hydroxy-1,2,3-propanetricarboxylic acid (citric acid); 1-hydroxy-1,2,3-propanetricarboxylic acid (isocitric acid); 1-hydroxy-1,2,4-butanetricarboxylic acid (homoisocitric acid); 2-hydroxy-3-hexadecyl-1,2,3-propanetricarboxylic acid (n-hexadecyl citric acid; agaricic acid).

(5) Miscellaneous Alpha Hydroxyacids: glyceruronic acid, erythruronic acid, threuronic acid; 2,3,4-trihydroxypentanuronic acids (isomers; riburonic acid, arabinuronic acid, xyluronic acid, lyxuronic acid); 2,3,4,5-tetrahydroxyhexanuronic acid (isomers; alluronic acid, altruronic acid, glucuronic acid, mannuronic acid, guluronic acid, iduronic acid, galacturonic acid, taluronic acid); 2,3,4,5,6-pentahydroxyheptanuronic acid (isomers; alloheptanuronic acid, altroheptanuronic acid, glucoheptanuronic acid, mannoheptanuronic acid, guloheptanuronic acid, idoheptanuronic acid, galactoheptanuronic acid, taloheptanuronic acid).

(B) Related Acids

The related acids are those hydroxyacids in which the hydroxyl group is at any carbon position other than the alpha position, or the hydroxyl group is replaced by a keto group, or other miscellaneous organic hydroxycarboxylic acids which are not readily represented by a generic structure. For convenience this group of compounds is subdivided into (1) beta and other hydroxyacids, (2) alpha ketoacids, (3) miscellaneous compounds, and (4) oligomers and polymers of hydroxyacids.

(1) Beta and other hydroxyacids: These hydroxyacids have a hydroxyl group at any carbon position other than the alpha carbon positions. Most common one is the beta hydroxyacid. Representative hydroxyacids are as follows: 3-hydroxypropanoic acid (beta-hydroxypropanoic acid), 3-hydroxybutanoic acid (beta-hydroxybutyric acid), 2-phenyl-3-hydroxypropanoic acid (tropic acid); 3-hydroxy-3,7,11-trimethyldodecanoic acid (trethocanic acid) and 9,10,16-trihydroxyhexadecanoic acid (aleuritic acid).

(2) Alpha Ketoacids: Ketoacids are related to hydroxyacids in that the hydroxyl group is replaced by the keto group. Although the keto group can be at any position other than the terminal ends, the preferred one is an alpha ketoacid. For example pyruvic acid, an alpha ketoacid is related to lactic acid in that the hydroxyl group of lactic acid is substituted by a keto group. In the skin, lactate dehydrogenase enzyme converts pyruvate to lactate and vice visa. The ketoacids have been found to have similar therapeutic effects as that of alpha hydroxyacids. The generic structure of alpha ketoacids may be represented as follows:

(R$_a$)COCOOH wherein R$_a$ is H, alkyl, aralkyl or aryl group of saturated or unsaturated, isomeric or non-isomeric, straight or branched chain or cyclic form, having 1 to 25 carbon atoms, and in addition R$_a$ may carry F, Cl, Br, I, OH, CHO, COOH and alkoxyl group having 1 to 9 carbon atoms. The alpha ketoacids may be present as a free acid or in a salt form with an organic base or an inorganic alkali. The typical alkyl, aralkyl, aryl and alkoxyl groups for R$_a$ include methyl, ethyl, propyl, isopropyl, butyl, pentyl, octyl, lauryl, stearyl, benzyl, phenyl, methoxyl and ethoxyl.

Representative alpha ketoacids which may be useful for cosmetic conditions and dermatologic indications are listed below: 2-ketoethanoic acid (glyoxylic acid), 2-ketopropanoic acid (pyruvic acid), 2-phenyl-2-ketoethanoic acid (benzoylformic acid), 3-phenyl-2-ketopropanoic acid (phenylpyruvic acid), 2-ketobutanoic acid, 2-ketopentanoic acid, 2-ketohexanoic acid, 2-ketoheptanoic acid, 2-ketooctanoic acid and 2-ketododecanoic acid.

(3) Miscellaneous Hydroxyacids: These hydroxyacids have similar therapeutic effects as that of alpha hydroxyacids but their chemical structures are not readily represented by the foregoing generic structures. These compounds are listed as follows: quinic acid (1,3,4,5-tetrahydroxycyclohexanecarboxylic acid), piscidic acid (4-hydroxybenzyltartaric acid), lactobionic acid (galactopyranosylgluconic acid), ascorbic acid (3-oxo-L-gulofuranolactone), Isoascorbic acid (D-erythro-hex-2-enonic acidr-lactone), 2-hexulosonic acids (isomers; arabino-2-hexulosonicacid, xylo-2-hexulosonic acid, ribo-2-hexulosonic acid, lyxo-2-hexulosonic acid), 5-hexulosonic acids (isomers; arabino-5-hexulosonic acid, xylo-5-hexulosonic acid, ribo-5-hexulosonic acid, lyxo-5-hexulosonic acid).

(4) Oligomers of Hydroxyacids: When two or more molecules of hydroxyacids either identical or non-identical are reacted chemically to each other, oligomers are formed. The chemical bond is usually an ester bond formed from the carboxyl group of one monomer and the hydroxyl group of a second monomer by eliminating a water molecule. In general, oligomers consist of 2 to 10 monomers of hydroxyacids. The oligomers may be cyclic or non-cyclic form or a mixture of the two. The generic structure of oligomers of hydroxyacids may be described as follows.

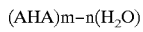

(AHA)m–n(H$_2$O)

wherein, AHA is a hydroxyacid described in previous Section VII, m=2–10, with a preferred number of 2–4, and n=m–1. AHA in each monomer may be identical or not identical. For example, glycolyl glycolate, glycolyl lactate, lactyl lactate and lactyl glycolate. Representative oligomers of AHA are listed below: glycolyl glycolate, lactyl lactate, citryl citrate, glycoly citrate, citryl glycolate, lactyl citrate, citryl lactate, malyl malate, malyl glycolate, tartaryl tartrate, tartaryl glycolate, glycolyl tartrate, glycolyl glycoly glycolate, lactyl lactyl lactate, and other AHA oligomers.

(C) Partial Salt and Lactone Forms

Alpha hydroxyacids and related acids may exist as free acid, partial salt and lactone forms. A partial salt is formed when an alpha hydroxyacid or related acid is partially neutralized with an organic or inorganic alkali. For example, glycolic acid 1 mole is reacted with ammonium hydroxide 0.5 mole. The reaction mixture thus formed consists of glycolic free acid 0.5 mole and ammonium glycolate 0.5 mole. When citric acid 1 mole is reacted with sodium hydroxide 1 mole the reaction mixture thus formed consists of citric acid monosodium salt 1 mole. Since citric acid has three carboxylic acid groups per molecule citric acid monosodium salt is a partial salt containing two free carboxylic acid groups and is still very acidic in nature.

Many alpha hydroxyacids and related acids may form intramolecular lactones. Some examples include gluconolactone, galactonolactone, glucuronolactone, galacturonolactone, gulonolactone, ribonolactone, saccharic acid lactone, pantoyllactone, glucoheptonolactone, mannonolactone, and galactoheptonolactone.

(VI) Enhanced Therapeutic Compositions

The molecular complex may be incorporated into a composition containing a biologically active topical agent to enhance its therapeutic effects. The topical agents include cosmetic and pharmaceutical agents. Since those agents are chemically distinct from alpha hydroxyacids and related acids (AHAs), their topical actions and effects are pharmacologically different from that of AHAs. In general, a combination of two topical agents may produce two. possibilities, namely (a) no enhancement or (b) enhancement or loss of therapeutic effect. In the case of (a) there is no substantial changes in topical effects of either agent, and the overall effects are due to added effects as predicted from both agents. In the case of (b) the enhanced or substantial loss of a therapeutic effect due to a combination of two agents is unpredictable.

We have discovered that when an AHA or its molecular complex is incorporated into a topical composition containing a cosmetic or pharmaceutical agent, therapeutic effects of such agent generally is enhanced. It appears that such enhancement is not mainly due to the enhanced penetration of the agent into the skin. Rather, the enhanced effects appear to suggest an increased affinity of a receptor molecule toward the agent in the skin. Cosmetic, pharmaceutical and topical agents include those that improve or eradicate age spots, keratoses and wrinkles; analgesics; anesthetics; anti-acne agents; antibacterials; antiyeast agents; antifungal agents; antiviral agents; antidandruff agents; antidermatitis agents; antipruritic agents; antiemetics; antimotion sickness agents; antiinflammatory agents; antihyperkeratolytic agents; antiperspirants; antipsoriatic agents; antiseborrheic agents; hair conditioners and hair treatment agents; antiaging and antiwrinkle agents; sunscreen agents; antihistamine agents; skin lightening agents; depigmenting agents; vitamins; corticosteroids; tanning agents; hormones; retinoids; topical cardiovascular agents and other dermatologicals.

Some examples of cosmetic and pharmaceutical agents are clotrimazole, ketoconazole, miconazole, griseofulvin, econazole, metronidazole, hydroxyzine, diphenhydramine, pramoxine, lidocaine, procaine, mepivacaine, monobenzone, erythromycin, tetracycline, clindamycin, meclocycline, hydroquinone, minocycline, naproxen, ibuprofen, theophylline, cromolyn, albuterol, retinoic acid, 13-cis retinoic acid, hydrocortisone, hydrocortisone 21-acetate, hydrocortisone 17-valerate, hydrocortisone 17-butyrate, betamethasone valerate, betamethasone dipropionate, triamcinolone acetonide, fluocinonide, clobetasol, propionate, benzoyl peroxide, crotamiton, propranolol, promethazine, salicylic acid, vitamin A acetate, vitamin A palmitate, vitamin E and vitamin E acetate. Others such agents will be readily apparent to skilled artisans.

(VII) Preparation of the Therapeutic Compositions

Topical compositions containing a molecular complex of the instant invention may be formulated as solution, gel, lotion, cream, ointment, shampoo, spray, stick, powder or other cosmetic and pharmaceutical preparations.

As discussed above, many complexing agents are commercially available as hydrochloride or other salt form. Accordingly, the salt can be first dissolved in a minimal amount of water, and the mixture is cooled externally with an ice-water bath. Sodium hydroxide or potassium hydroxide solution in equal molar amount then can be slowly added to generate the complexing agent as a free base from.

In one method of preparation, a complexing agent such as amino acid ester, amino acid amide, aminosaccharide, aminoalditol or aminocyclitol in aqueous solution is cooled externally with an ice-water bath. An alpha hydroxyacid or related acid is slowly added to the mixture with stirring to initiate the formation of a molecular complex, as indicated by a continuous decrease in pH of the reaction mixture. Alternatively, for example, the process may be reversed by adding a complexing agent to a solution containing an alpha hydroxyacid or related acid to form a molecular complex, as indicated by a continuous increase in pH of the reaction mixture. Completion of the reaction is manifested by the end of any pH change of the reaction mixture.

To prepare a solution composition ethanol, propylene glycol, butylene glycol, other higher alcohols and cosmetically or pharmaceutically acceptable vehicle may be added to the above aqueous mixture which contains the molecular complex.

The concentration of the complexing agent may range from 0.01 to 99.9%, with preferred concentration of from about 0.1 to 50% and with more preferred concentration of from about 1 to 25% by weight of the total composition. Other advantageous concentration ranges provide at least being at least 3%, 4% or 5% of a complexing agent. Higher concentrations of a complexing agent in the ranges of 40%, 50%, 60% or more also can be employed. Thus, acceptable ranges of a complexing agent will be from about 1%, 2%, 3%, 4% or 5% at the minimum to about 95% at maximum, and within that range will be ranges of from about 1% to about 5%, from about 5% to about 10%, from about 10% to about 20%, from about 20% to about 40%, from about 40% to about 60%, from about 60% to about 80%, from about 80% to about 95%. These weights are based on the weight of the total composition.

The concentration of the alpha hydroxyacid or the related acid may range from 0.01 to 99.9%. Advantageous concentrations will comprise at least 0.2% alpha hydroxyacid or related acid, is and typically at least about 1% or 2% of alpha hydroxyacid or related acid. Other advantageous concentration ranges provide at least being at least 3%, 4% or 5% of an alpha hydroxyacid or related acid. Higher concentrations of an alpha hydroxyacid or related acid in the ranges of 40%, 50%, 60% or more also can be employed. Thus, typical ranges of an alpha hydroxyacid or related acid will be from about 1%, 2%, 3%, 4% or 5% at the minimum to 100% at maximum, and within that range will be ranges of from about 5% to about 10%, from about 10% to about 20%, from about 20% to about 40%, from about 40% to about 60%, from about 60% to about 80%, from about 80% to about 100%. These weights are based on the weight of the total composition.

To prepare a topical composition in lotion, cream or ointment form, the above aqueous mixture containing the molecular complex is mixed in a conventional manner with a commonly available lotion, cream or ointment base. Concentrations of the complexing agent and AHA are the same as described above. A topical composition of the instant invention may also be formulated in a gel form. A typical gel composition is formulated by the addition of a gelling agent such as methyl cellulose, ethyl cellulose, hydroxyethylcellulose, hydroxypropylcellulose, hydroxypropylmethylcellulose, carbomer or ammonium glycyrrhizate to a solution mixture containing the molecular complex. The preferred concentration of the gelling agent may range from 0.1 to 4 percent by weight of the total composition. Concentrations of the complexing agent and AHA are the same as described above.

To prepare a combination composition in a cosmetically or pharmaceutically acceptable vehicle, a cosmetic, pharmaceutical or topical agent is incorporated into any one of the above composition by dissolving or mixing the agent into the formulation.

The following are illustrative examples of formulations and testings according to this invention. Although the examples utilize only selected compounds and formulations, it should be understood that the following examples are illustrative and not limited. Therefore, any of the aforementioned complexing agents and alpha hydroxyacids or related acids may be substituted according to the teachings of this invention in the following example.

EXAMPLE 1

A complexing agent of an amino acid ester in free base may be prepared from its salt as follows.

Glycine ethyl ester hydrochloride 14 g (0.1 mole) was dissolved in water 20 ml and the mixture was cooled externally with an ice-water bath. Sodium hydroxide 5N solution 20 ml was slowly added to the above mixture with stirring. The clear solution 52 ml (55 g) thus obtained had pH 9.6 and contained 100 mmole of glycine ethyl ester in free base form. The complexing agent thus obtained was used immediately for preparation of a molecular complex with an alpha hydroxyacid or related acid in the following Examples.

EXAMPLE 2

A molecular complex containing glycine ethyl ester and glycolic acid in cream form was formulated as follows.

Glycine ethyl ester 1.03 g (10 mmole) in 5.2 ml aqueous solution prepared according to Example 1 was cooled externally in an ice-water bath. Glycolic acid 70% aqueous solution 2.2 g containing 1.52 g (20 mmole) 2-hydroxyethanoic acid was slowly added to the above mixture with stirring. A molecular complex was formed immediately as shown by the decrease in pH from 9.6 to 3.5. The clear solution 7.7 g containing the molecular complex was then mixed with an oil-in-water emulsion 12.3 g. The cream thus formulated had pH 3.6 and contained 7.6% 2-hydroxyethanoic acid and 5.2% glycine ethyl ester in a molar ratio of 2 to 1.

EXAMPLE 3

A molecular complex containing glycine ethyl ester and lactic acid in cream form was formulated as follows.

Glycine ethyl ester 1.03 g (10 mmole) in 5.2 ml aqueous solution prepared according to Example 1 was cooled externally in an ice-water bath. DL-Lactic acid 90% solution 2.0 g containing 1.8 g (20 mmole) 2-hydroxypropanoic acid was slowly added to the above mixture with stirring. A molecular complex was formed immediately as shown by the decrease in pH from 9.6 to 3.8. The clear solution 7.5 g containing the molecular complex was then mixed with an oil-in-water emulsion 12.5 g. The cream thus formulated had pH 4.0 and contained 9% 2-hydroxypropanoic acid and 5.2% glycine ethyl ester in a molar ratio of 2 to 1.

EXAMPLE 4

A molecular complex containing glycine ethyl ester and citric acid in cream form was formulated as follows.

Glycine ethyl ester 1.03 g (10 mmole) in 5.2 ml aqueous solution prepared according to Example 1 was cooled externally in an ice-water bath. Citric acid monohydrate 2.1 g containing 1.92 g (10 mmole) citric acid was slowly added to the above mixture with stirring. A molecular complex was formed immediately as shown by the decrease in pH from 9.6 to 3.0. The clear solution 7.6 g containing the molecular complex was then mixed with an oil-in-water emulsion 12.4 g. The cream thus formulated had pH 3.4 and contained 9.6% citric acid and 5.2% glycine ethyl ester in a molar ratio of 1 to 1.

EXAMPLE 5

A molecular complex containing glycine ethyl ester and methyllactic acid in cream form was formulated as follows.

Glycine ethyl ester 1.03 g (10 mmole) in 5.2 ml aqueous solution prepared according to Example 1 was cooled externally in an ice-water bath. Methyllactic acid 2.1 g (20 mmole) was slowly added to the above mixture with stirring. A molecular complex was formed immediately as shown by the decrease in pH from 9.6 to 3.8. The clear solution 7.6 g containing the molecular complex was then mixed with an oil-in-water emulsion 12.4 g. The cream thus formulated had pH 3.9 and contained 10.5% 2-methyl-2-hydroxypropanoic acid and 5.2% glycine ethyl ester in a molar ratio of 2 to 1.

EXAMPLE 6

A molecular complex containing glycine ethyl ester and malic acid in cream form was formulated as follows.

Glycine ethyl ester 1.03 g (10 mmole) in 5.2 ml aqueous solution prepared according to Example 1 was cooled externally in an ice-water bath. Malic acid 2.7 g (20 mmole) and water 5 ml were slowly added to the above mixture with stirring. A molecular complex was formed immediately as shown by the decrease in pH from 9.6 to 2.8. The clear solution 13.2 g containing the molecular complex was then mixed with an oil-in-water emulsion 11.8 g. The cream thus formulated had pH 3.0 and contained 10.8% malic acid and 4.1% glycine ethyl ester in a molar ratio of 2 to 1.

EXAMPLE 7

A molecular complex containing glycine ethyl ester and gluconolactone in cream form was formulated as follows.

Glycine ethyl ester 1.03 g (10 mmole) in 5.2 ml aqueous solution prepared according to Example 1 was cooled externally in an ice-water bath. Gluconolactone 7.2 g (40 mmole) and water 15 ml were slowly added to the above mixture with stirring. A molecular complex was formed immediately as shown by the decrease in pH from 9.6 to 2.6. The clear solution 27.7 g containing the molecular complex was then mixed with an oil-in-water emulsion 47.3 g. The cream thus formulated had pH 2.6 and contained 9.6% gluconolactone and 1.4% glycine ethyl ester in a molar ratio of 4 to 1.

EXAMPLE 8

A complexing agent of an amino acid amide in free base may be prepared from its salt as follows.

Glycinamide hydrochloride 11.1 g (0.1 mole) was dissolved in water 20 ml and the mixture was cooled externally with an ice-water bath. Sodium hydroxide 5N solution 20 ml was slowly added to the above mixture with stirring. The clear solution 50 ml (54 g) thus obtained had pH 10.8 and contained 100 mmole of glycinamide in free base form. The complexing agent thus obtained was used for preparation of a molecular complex with an alpha hydroxyacid or related acid in the following Examples.

EXAMPLE 9

A molecular complex containing glycinamide and glycolic acid in cream form was formulated as follows.

Glycinamide 0.74 g (10 mmole) in 5 ml aqueous solution prepared according to Example 8 was cooled externally in an ice-water bath. Glycolic acid 70% aqueous solution 2.2 g containing 1.52 g (20 mmole) 2-hydroxyethanoic acid was slowly added to the above mixture with stirring. A molecular complex was formed immediately as shown by the decrease in pH from 10.8 to 3.7. The clear solution 7.6 g containing the molecular complex was then mixed with an oil-in-water emulsion 12.4 g. The cream thus formulated had pH 3.8 and contained 7.6% 2-hydroxyethanoic acid and 3.7% glycinamide in a molar ratio of 2 to 1.

EXAMPLE 10

A molecular complex containing glycinamide and lactic acid in cream form was formulated as follows.

Glycinamide 0.74 g (10 mmole) in 5 ml aqueous solution prepared according to Example 8 was cooled externally in an ice-water bath. DL-Lactic acid 90% solution 2.0 g containing 1.8 g (20 mmole) 2-hydroxypropanoic acid was slowly added to the above mixture with stirring. A molecular complex was formed immediately as shown by the decrease in pH from 10.8 to 3.9. The clear solution 7.4 g containing the molecular complex was then mixed with an oil-in-water emulsion 12.6 g. The cream thus formulated had pH 4.0 and contained 9% 2-hydroxypropanoic acid and 3.7% glycinamide in a molar ratio of 2 to 1.

EXAMPLE 11

A molecular complex containing glycinamide and citric acid in cream form was formulated as follows.

Glycinamide 0.74 g (10 mmole) in 5 ml aqueous solution prepared according to Example 8 was cooled externally in an ice-water bath. Citric acid monohydrate 2.1 g containing 1.92 g (10 mmole) citric acid was slowly added to the above mixture with stirring. A molecular complex was formed immediately as shown by the decrease in pH from 10.8 to 3.1. The clear solution 7.5 g containing the molecular complex was then mixed with an oil-in-water emulsion 12.5 g. The cream thus formulated had pH 3.5 and contained 9.6% citric acid and 3.7% glycinamide in a molar ratio of 1 to 1.

EXAMPLE 12

A molecular complex containing glycinamide and methyllactic acid in cream form was formulated as follows.

Glycinamide 0.74 g (10 mmole) in 5 ml aqueous solution prepared according to Example 8 was cooled externally in an ice-water bath. Methyllactic acid 2.1 g (20 mmole) was slowly added to the above mixture with stirring. A molecular complex was formed immediately as shown by the decrease in pH from 10.8 to 4.0. The clear solution 7.5 g containing the molecular complex was then mixed with an oil-in-water emulsion 12.5 g. The cream thus formulated had pH 4.1 and contained 10.5% 2-methyl-2-hydroxypropanoic acid and 3.7% glycinamide in a molar ratio of 2 to 1.

EXAMPLE 13

A molecular complex containing glycinamide and malic acid in cream form was formulated as follows.

Glycinamide 0.74 g (10 mmole) in 5 ml aqueous solution prepared according to Example 8 was cooled externally in an ice-water bath. Malic acid 2.7 g (20 mmole) was slowly added to the above mixture with stirring. A molecular complex was formed immediately as shown by the decrease in pH from 10.8 to 2.8. The clear solution 8.1 g containing the molecular complex was then mixed with an oil-in-water emulsion 11.9 g. The cream thus formulated had pH 3.2 and contained 13.5% malic acid and 3.7% glycinamide in a molar ratio of 2 to 1.

EXAMPLE 14

A molecular complex containing glycinamide and gluconolactone in cream form was formulated as follows.

Glycinamide 0.74 g (10 mmole) in 5 ml aqueous solution prepared according to Example 8 was cooled externally in an ice-water bath. Gluconolactone 7.2 g (40 mmole) and water 10 ml were slowly added to the above mixture with stirring. A molecular complex was formed immediately as shown by the decrease in pH from 10.8 to 3.0 The clear solution 22.6 g containing the molecular complex was then mixed with an oil-in-water emulsion 27.4 g. The cream thus formulated had pH 3.0 and contained 14.4% gluconolactone and 1.5% glycinamide in a molar ratio of 4 to 1.

EXAMPLE 15

A complexing agent of an aminosaccharide, aminoalditol or aminocyclitol in free base form may be prepared from its hydrochloride or other salt as follows. D(+)-Glucosamine hydrochloride 21.6 g was dissolved in water 30 ml and the mixture was cooled externally with an ice-water bath. Sodium hydroxide 5N solution 20 ml was slowly added to the above mixture with stirring. The clear solution 70 ml (82 g) thus obtained had pH 8.7 and contained 100 mmole of D(+)-glucosamine in free base form. D(+)-Glucosamine thus obtained was used for the preparation of molecular complex with an alpha hydroxyacid or related compound in the following Examples. D(+)-Glucosamine without a molecular complex formation was also used in the formulation for topical application to the skin. D-Galactosamine and D-mannosamine prepared in the same manner from their hydrochloride salts were used for the formulation of molecular complex with an alpha hydroxyacid or related compound.

EXAMPLE 16

Molecular complex containing glycolic acid and glucosamine in cream form was formulated as follows.

D(+)-Glucosamine 3.6 g (20 mmole) in 14 ml aqueous solution prepared according to Example 15 was cooled externally in an ice-water bath. Glycolic acid 70% aqueous solution 4 ml containing 3.6 g (46 mmole) 2-hydroxyethanoic acid was slowly added to the above mixture with stirring. A molecular complex was formed immediately as shown by the decrease in pH from 8.7 to 2.6. The clear solution 20.8 g containing the molecular complex was then mixed with an oil-in-water emulsion 79.2 g. The cream thus formulated had pH 3.0 and contained 3.6% each of 2-hydroxyethanoic acid and glucosamine in a molar ratio of 2.3 to 1.

EXAMPLE 17

Molecular complex containing glycolic acid and glucosamine in solution form was formulated as follows.

D(+)-Glucosamine 5.37 g (30 mmole) in 21 ml aqueous solution prepared according to Example 15 was cooled externally in an ice-water bath. Glycolic acid 70% aqueous solution 28.3 ml containing 25.2 g (332 mmole) 2-hydroxyethanoic acid was slowly added to the above mixture with stirring. A molecular complex was formed immediately as shown by the decrease in pH from 8.7 to 2.5. Ethanol 30.7 ml and propylene glycol 20 ml were added. The solution composition thus formulated had pH 2.6 and contained 25% 2-hydroxyethanoic acid and 5.4% glucosamine in a molar ratio of 11 to 1.

EXAMPLE 18

Molecular complex containing lactic acid and glucosamine in cream form was formulated as follows.

D(+)-Glucosamine 7.16 g (40 mmole) in 28 ml aqueous solution prepared according to Example 15 was cooled externally in an ice-water bath. DL-Lactic acid 90% solution 12 ml containing 13 g (144 mmole) DL-2-hydroxypropanoic acid was slowly added to the above mixture with stirring. A molecular complex was formed immediately as shown by the decrease in pH from 8.7 to 2.6. The clear solution 44 g containing the molecular complex was then mixed with an oil-in-water emulsion 56 g. The cream thus formulated had pH 2.6 and contained 13% 2-hydroxypropanoic acid and 7.2% glucosamine in a molar ratio of 3.6 to 1.

EXAMPLE 19

Molecular complex containing lactic acid and glucosamine in solution form was formulated as follows.

D(+)-Glucosamine 5.4 g (30 mmole) in 21 ml aqueous solution prepared according to Example 15 was cooled externally in an ice-water bath. DL-Lactic acid 90% solution 26 ml containing 25 g (280 mmole) DL-2-hydroxypropanoic acid was slowly added to the above mixture with stirring. A molecular complex was formed immediately as shown by the decrease in pH from 8.7 to 3.0. Water 11 ml, ethanol 20 ml and propylene glycol 20 ml were added to the mixture. The solution composition thus formulated had pH 3.1 and contained 25% 2-hydroxypropanoic acid and 5.4% glucosamine in a molar ratio of 9.3 to 1.

EXAMPLE 20

Molecular complex containing gluconolactone and glucosamine in cream form was formulated as follows.

D(+)-Glucosamine 1.8 g (10 mmole) in 7 ml aqueous solution prepared according to Example 15 was cooled externally in an ice-water bath. Gluconolactone 7.5 g (42 mmole) in water 5 ml was slowly added to the above mixture with stirring. A molecular complex was formed immediately as shown by the decrease in pH from 8.7 to 2.4. The clear solution 20.7 g containing the molecular complex was then mixed with an oil-in-water emulsion 30 g. The cream thus formulated had pH 2.7 and contained 14.8% gluconolactone and 3.6% glucosamine in a molar ratio of 4.2 to 1.

EXAMPLE 21

Molecular complex containing gluconic acid and glucosamine in solution form was formulated as follows.

D(+)-Glucosamine 3.6 g (20 mmole) in 14 ml aqueous solution prepared according to Example 15 was cooled externally in an ice-water bath. Gluconic acid 50% aqueous solution 50 g (140 mmole) was slowly added to the above mixture with stirring. A molecular complex was formed immediately as shown by the decrease in pH from 8.7 to 3.0. Ethanol 16 ml and propylene glycol 20 ml were added to the mixture. The solution composition thus formulated had pH 3.0 and contained 25% gluconic acid and 3.6% glucosamine in a molar ratio of 7 to 1.

EXAMPLE 22

Molecular complex containing citric acid and glucosamine in cream form was formulated as follows.

D(+)-Glucosamine 1.8 g (10 mmole) in 7 ml aqueous solution prepared according to Example 15 was cooled externally in an ice-water bath. Citric acid 2 g (10 mmole) was slowly added to the above mixture with stirring. A molecular complex was formed immediately as shown by the decrease in pH from 8.7 to 2.5. The clear solution 10.2 g containing the molecular complex was then mixed with an oil-in-water emulsion 15 g. The cream thus formulated had pH 2.5 and contained 7.8% citric acid and 7% glucosamine in a molar ratio of 1 to 1.

EXAMPLE 23

Molecular complex containing citric acid and glucosamine in solution form was formulated as follows.

D(+)-Glucosamine 7.2 g (40 mmole) in 28 ml aqueous solution prepared according to Example 15 was cooled externally in an ice-water bath. Citric acid 25 g (130 mmole) and water 20 ml were slowly added to the above mixture with stirring. A molecular complex was formed immediately as shown by the decrease in pH from 8.7 to 2.3. Ethanol 7ml and propylene glycol 20 ml were added to the mixture. The solution composition thus formulated had pH 2.3 and contained 25% citric acid and 7.2% glucosamine in a molar ratio of 3.3 to 1.

EXAMPLE 24

Molecular complex containing methyllactic acid and glucosamine in solution form was formulated as follows.

D(+)-Glucosamine 5.4 g (30 mmole) in 21 ml aqueous solution prepared according to Example 15 was cooled externally in an ice-water bath. 2-Methyl-2-hydroxypropanoic acid 25 g (240 mmole) and water 20 ml were slowly added to the above mixture with stirring. A molecular complex was formed immediately as shown by the decrease in pH from 8.7 to 3.4. Ethanol 14 ml and propylene glycol 20 ml were added to the mixture. The solution composition thus formulated had pH 3.4 and contained 25% 2-methyl-2-hydroxypropanoic acid and 5.4% glucosamine in a molar ratio of 8 to 1.

EXAMPLE 25

Molecular complex containing Isoascorbic acid and glucosamine in cream form was formulated as follows.

D(+)-Glucosamine 1.8 g (10 mmole) in 7 ml aqueous solution prepared according to Example 15 was cooled externally in an ice-water bath. D(−)-Isoascorbic acid 4 g (22.7 mmole) and water 5 ml were slowly added to the above mixture with stirring. A molecular complex was formed immediately as shown by the decrease in pH from 8.7 to 2.9. The clear solution 17 g containing the molecular complex was then mixed with an oil-in-water emulsion 40 g. The cream thus formulated had pH 3.1 and contained 7% isoascorbic acid and 3% glucosamine in a molar ratio of 2.3 to 1.

EXAMPLE 26

Molecular complex containing lactobionic acid and glucosamine in cream form was formulated as follows.

D(+)-Glucosamine 1.8 g (10 mmole) in 7 ml aqueous solution prepared according to Example 15 was cooled externally in an ice-water bath. Lactobionic acid 8 g (22.3 mmole) and water 5 ml were slowly added to the above mixture with stirring. A molecular complex was formed immediately as shown by the decrease in pH from 8.7 to 3.5. The clear solution 21 g containing the molecular complex was then mixed with an oil-in-water emulsion 29 g. The cream thus formulated had pH 3.5 and contained 16% lactobionic acid and 3.6% glucosamine in a molar ratio of 2.2 to 1.

EXAMPLE 27

Molecular complex containing pyruvic acid and glucosamine in cream form was formulated as follows.

D(+)-Glucosamine 1.8 g (10 mmole) in 7 ml aqueous solution prepared according to Example 15 was cooled externally in an ice-water bath. Pyruvic acid 1 ml (14.4 mmole) was slowly added to the above mixture with stirring. A molecular complex was formed immediately as shown by the decrease in pH from 8.7 to 1.8. The clear solution 9.5 g containing the molecular complex was then mixed with an oil-in-water emulsion 25 g. The cream thus formulated had pH 2.0 and contained 3.8% pyruvic acid and 5.2% glucosamine in a molar ratio of 1.4 to 1.

EXAMPLE 28

A molecular complex containing an alpha hydroxyacid lactone and an amino acid amide in a gel composition was formulated as follows.

A complexing agent solution 12.1 g containing glycinamide 1.7 g (22.4 mmole) prepared according to Example 8 was cooled externally in an ice-water bath. Gluconolactone 10 g (56 mmole), propylene glycol 12 ml, ethanol 10 ml and water 67 ml were slowly added to the above mixture with stirring. Chitosan 1 g was added and the mixture was homogenized at room temperature until a uniform gel was obtained. The gel thus formulated had pH 3.8 and contained 9% gluconolactone and 1.4% glycinamide in a molar ratio of 2.5 to 1.

EXAMPLE 29

A molecular complex containing an alpha hydroxyacid and an amino acid ester incorporated with a cosmetic, pharmaceutical or other topical agent was formulated as follows.

Glycine ethyl ester 1.03 g (10 mmole) in 5.2 ml aqueous solution prepared according to Example 1 was cooled externally in an ice-water bath. Glycolic acid 70% aqueous solution 2.2 g containing 1.52 g (20 mmole) 2-hydroxyethanoic acid was slowly added to the above mixture with stirring. A molecular complex was formed immediately as shown by the decrease in pH from 9.6 to 3.5. The clear solution 7.7 g containing the molecular complex was then mixed with an oil-in-water emulsion 12.3 g, retinyl acetate 4 g and tocopheryl acetate 4 g. The light yellowish cream thus formulated had pH 3.4 and contained 7% glycolic acid and 4.8% glycine ethyl ester in a molar ratio of 2 to 1, and also contained 3.7% vitamin A acetate and 3.7% vitamin E acetate.

EXAMPLE 30

A molecular complex containing gluconolactone and glycinamide incorporated with a sunscreen agent in cream form was formulated as follows.

Glycinamide 0.74 g (10 mmole) in 5 ml aqueous solution prepared according to Example 8 was cooled externally in an ice-water bath. Gluconolactone 7.2 g (40 mmole) and water 10 ml were slowly added to the above mixture with stirring. A molecular complex was formed immediately as shown by the decrease in pH from 10.8 to 3.0 The clear solution 22.6 g containing the molecular complex was then mixed with an oil-in-water emulsion 27.4 g and octyl methoxycinnamate 6.7 g. The cream thus formulated had pH 2.7 and contained 12.7% gluconolactone and 1.3% glycinamide in a molar ratio of 4 to 1, and also contained 11.8% octyl methoxycinnamate.

EXAMPLE 31

Skin thickness was measured as follows.

A test composition containing a molecular complex prepared according to the above Examples was topically applied twice daily to the left forearm, and a control vehicle was applied in the same manner to the right forearm for a specified period of time. The skin was grasped with a 2×6 cm metal hinge, the internal faces of which were coated with emery cloth to prevent skin slippage, and was manually squeezed to threshold patient discomfort. Triplicate measurements of skin thickness on each forearm were done, and average numbers were obtained. Combined thickness of two whole-skin layers including thickness of the two hinge leaves was measured with NSK engineering micrometer calipers. Thickness of the two hinge leaves was subtracted to determine actual 2 skin layer thickness. The sites measured were 5 cm distal to the ante-cubital fold over the dorsal ante-brachio-radialis muscles.

EXAMPLE 32

A male, age 70, topically applied twice daily a cream containing the molecular complex as described in Example 22 to his left forearm for two weeks. He applied a control vehicle in the same manner to his right forearm. Skin thickness was measured at baseline and also at the end of two weeks according to Example 31. It was found that the skin of the left forearm increased in thickness approximately 21%, while there was no change in the skin thickness of his right forearm. This suggested that the molecular complex of the instant invention on topical application had stimulated biosynthesis of dermal components which include glycosaminoglycans, collagen and/or elastic fibers. Such increase in skin thickness are beneficial for topical management and/or treatment of skin changes associated with aging.

EXAMPLE 33

A female, age 66, topically applied twice daily a composition containing the molecular complex as described in Example 23 to her left forearm for two weeks. She applied a control vehicle in the same manner to her right forearm. Skin thickness was measured at baseline and also at the end of two weeks according to Example 14. It was found that the skin of the left forearm increased in thickness approximately 48%, while there was a slight decrease of 1.4% in the skin thickness of her right forearm. This suggests that the molecular complex of the instant invention on topical application has stimulated biosynthesis of dermal components which include glycosaminoglycans, collagen and/or elastic fibers. Such increase in skin thickness are beneficial for topical management and/or treatment of skin changes associated with aging.

Test Results

Some test results have been described specifically in the foregoing Examples. In general, recruited volunteers and patients participated in these studies. Participating subjects were given topical formulations containing an active ingredient in the form of a molecular complex, and if necessary vehicle control formulations for comparison. In comparison studies the active formulation was topically applied to one side of the body such as side of face, forearm, leg; and the control vehicle was applied to same area on the opposite side of the body. In the sequential comparison, the active formulation was topically applied for a week followed by the vehicle control for example in studies on pruritus. Applications were also made one to several times daily for tests on various cosmetic conditions and dermatologic indications including dry skin, xerosis, palmar and plantar hyperkeratoses, pseudofolliculitis barbae, ichthyosis, acne, eczema, psoriasis, pruritus, warts, age spots, lentigines, melasmas, blemished skin, fine lines, wrinkles, and the skin changes associated with aging. The following are some examples of such tests.

1. Common dry skin

Patients and subjects having ordinary dry skin or with moderate degrees of dry skin as evidenced by dryness, flaking and cracking of the skin were instructed to apply topically the active formulations on the affected areas of the skin. Topical applications twice daily were continued for two to four weeks. In all the 8 subjects tested, the feeling of the skin dryness disappeared within a week of topical application without any detectable signs of irritation. The rough and cracked skin became less pronounced and the skin appeared normal and smooth. Once restored to normal, the skin remained improved for some time until causes of dry skin, such as low humidity, cold weather, wind, excessive contact pressure, detergents, soaps, solvents and chemicals again caused recurrence of the dry skin condition. On continued use it was also found that twice daily topical application of a formulation containing an active molecular complex of the instant invention could prevent the development of new dry skin lesions.

2. Ichthyosis

Ichthyotic skin is different from ordinary dry skin because the former is an inherited genetic disease. The involved skin is hyperplastic, fissured and has thick adherent "fish like" scales. The degree of thickening is such that lesions are palpably and visually elevated. The thickened adherent scales cause the surface of involved skin to be markedly rough and uneven. These two attributes of thickness and texture can be quantified to allow objective measurement of degree of improvement from topically applied test formulations. By means of such parameters, degrees of change in lesions can be recorded and comparisons made of one treated site to another.

Three patients having ichthyotic skin conditions were tested with vehicle control and formulations containing an active molecular complex. Test areas were of a size convenient for topical applications, i.e., circles 5 cm in diameter demarcated with a plastic ring of that size inked on a stamp pad. The formulations were topically applied by the patient in an amount sufficient to cover the treatment sites. Applications were made twice daily and without occlusive dressings.

In contrast to vehicle control with minimal improvement, all the test sites of the active formulations showed marked reduction of roughness, thickness and scales after a week of topical application. The skin appeared smooth and normal without irritation after one to four weeks of topical application with the formulations containing an active molecular complex of the instant invention.

3. Psoriasis

Psoriasis is an inherited genetic disease. The involved skin in psoriasis is hyperplastic (thickened), erythematous (red or inflamed), and has thick adherent scales. The degree of thickening is such that lesions are elevated up to 1 mm above the surface of adjacent normal skin; erythema is usually an intense red; the thickened adherent scales cause the surface of involved skin to be markedly rough and uneven. These three attributes of thickness, color and texture can be quantified to allow objective measurement of degree of improvement from topically applied test formulations. By means of such parameters, degree of improvement in psoriatic lesions can be recorded and comparisons made of one treated site to another.

Four patients having psoriasis participated in this study. Test areas were kept to minimal size convenient for topical application, i.e., circles approximately 4 cm in diameter. The formulations containing a corticosteroid with or without a molecular complex of the instant invention were topically applied by the patient in an amount (usually 0.1 milliliter) sufficient to cover the test site. Applications were made twice daily and without occlusive dressings. Test periods usually lasted for two to four weeks.

It was found that formulations containing a corticosteroid in a molecular complex were more effective and encountered less tachyphylaxis (drug resistance) than that of corticosteroid alone. The skin became smooth and normal in appearance after four weeks of topical application with the formulations containing a corticosteroid in a molecular complex of the instant invention.

4. Eczema

Eczema is an inflammatory skin disease characterized by various ranges of redness, vesiculation, infiltration, watery discharge, local itching and burning, scales and crusts. Three patients having chronic eczema participated in this study. The subjects were provided with two formulations: the first one containing a corticosteroid for the right side of the body, and the second one a corticosteroid in a molecular complex of the instant invention for the left side of the body. The formulations were topically applied to the lesions three times daily.

It was found that while the formulations containing a corticosteroid moderately improved the skin lesions, the formulations containing the corticosteroid in the molecular complex of the instant invention obliterated clinical evidence of eczema lesions without skin irritation.

5. Acne

Five patients having comedogenic lesions and moderate acne on the face participated in this study. Each patient received two formulations: the first one containing salicylic acid and the second one containing salicylic acid in a molecular complex of the instant invention. Each participating patient was instructed to apply topically the first formulation on the right side of the face and the second one on the left side of the face. Three times daily administration was continued for 8 to 12 weeks. The degree and rate of improvement on acne lesions were clinically evaluated. It was found that while the acne lesions on the right side of the face improved slightly most lesions on the left side of the face were eradicated after 12 weeks of topical application with the formulations of the instant invention.

It was also found that for papulopustular and/or pustular acne, a molecular complex containing a retinoid or antibiotic was therapeutically more effective in eradicating acne lesions than the retinoid or antibiotic alone. These antiacne agents may include retinoic acid, retinyl acetate, erythromycin, tetracycline, clindamycin, meclocycline and minocycline.

6. Pigmented and Non-pigmented Spots and Lesions

Many pigmented and non-pigmented spots and patches on the face and the back of the hands consist of age spots, keratoses, freckles, melasma, chloasma and lentigines. Seven volunteer subjects having such spots and patches on the face participated in this study. Each subject was provided with two formulations: the first one containing hydroquinone and the second one containing hydroquinone in a molecular complex of the instant invention. The first formulation was topically applied on the right side of the face, and the second one on the left side of the face. Twice daily application was continued for 3 to 6 months.

It was found that while the formulations containing hydroquinone improved very slightly on the right side of the face, the formulations containing hydroquinone in the molecular complex of the instant invention eradicated most pigmented and non-pigmented spots and patches at the end of 6 months.

7. Athlete's Foot and Nail Infections

Fungal infections of finger and toe nails are more difficult to treat as compared to that of skin infections. Most antifungal agents such as clotrimazole, miconazole, ketoconazole and griseofulvin are not bioavailable in the commonly used topical preparations for penetration through the nail plate. Four Patients having nail infections participated in this study. Each subject was provided with two formulations: the first one containing an antifungal agent and the second one containing an antifungal agent in a molecular complex of the instant invention.

The first formulation was topically applied to the infected nails of the right hand and/or foot, and the second one to that of left hand and/or foot. Twice daily applications were continued for 3 to 6 months.

It was found that while the formulations containing an antifungal agent had a minimal effect on the fungal infections of the nails, the formulations containing an antifungal agent in the molecular complex substantially improved most fungal infections of the nails at the end of 6 months.

8. Fine Lines and Wrinkles

Fine lines and wrinkles on the face, neck, and other parts of the body are due to intrinsic and/or extrinsic aging including photoaging. Fifteen volunteers and patients participated in this study. Each subject was provided with a formulation containing a molecular complex of the instant invention, and twice daily topical application was made to affected areas of the skin for 6 to 12 months.

It was found that the formulations containing the molecular complex of the instant invention were topically effective in improving fine lines and wrinkles at the end of a 6 month period. Continued and sustained use of the formulations have been found to substantially improve most fine lines and wrinkles at the end of 12 months.

What is claimed is:

1. A composition comprising:
   A. an alpha hydroxyacid or related acid; and
   B. an organic complexing agent comprising either:
      (i) one or more amnino groups. and one or more other functional groups that are capable of forming multiple intermolecular hydrogen bonds with the hydroxyl groups of a free alpha hydroxyacid or related acid, wherein said complexing agent is an aminosaccharide; or
      (ii) one or more amino groups, and one or more other functional groups that are capable of forming multiple intermolecular hydrogen bonds with the hydroxyl groups of a free alpha hydroxyacid or related acid, wherein said complexing agent is a monomer.

2. A composition according to claim 1, wherein said composition comprises an alpha hydroxyacid selected from the group consisting of compounds of the formula:

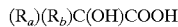

where $R_a$ and $R_b$ are H, F, Cl, Br, I, alkyl, aralkyl or aryl group of saturated or unsaturated, isomeric or non-isomeric, straight or branched chain or cyclic form, having 1 to 25 carbon atoms, and in addition $R_a$ and $R_b$ may carry OH, CHO, COOH and alkoxyl group having 1 to 9 carbon atoms, and wherein the hydrogen atom attached to the carbon atom may be substituted by F, Cl, Br, I, or lower alkyl, aralkyl, aryl or alkoxyl group having 1 to 9 carbon atoms, and wherein the alpha hydroxyacids may be present as a free acid or lactone form, or in a partial salt form with an organic base or an inorganic alkali, and wherein the alpha hydroxyacid may exist as a stereoisomer in D, L, and DL forms when Ra and Rb are not identical.

3. A composition according to claim 2, wherein Ra and Rb are independently selected from the group consisting of hydrogen, methyl, ethyl, propyl, isopropyl, butyl, pentyl, octyl, decyl, dodecyl, hexadecyl, benzyl, and phenyl.

4. A composition according to claim 2, wherein said alpha hydroxyacid is an alkyl alpha hydroxyacid selected from the group consisting of 2-hydroxyethanoic acid (glycolic acid), 2-hydroxypropanoic acid (lactic acid), 2-methyl 2-hydroxypropanoic acid (methyllactic acid), 2-hydroxybutanoic acid, 2-hydroxypentanoic acid, 2 -hydroxyhexanoic acid, 2 -hydroxyheptanoic acid, 2-hydroxyoctanoic acid, 2-hydroxynonanoic acid, 2-hydroxydecanoic acid, 2-hydroxyundecanoic acid, 2-hydroxydodecanoic acid, 2-hydroxytetradecanoic acid, 2-hydroxyhexadecanoic acid, 2-hydroxyoctadecanoic acid, 2-hydroxyeicosanoic acid (alpha hydroxyarachidonic acid), 2-hydroxytetraeicosanoic acid (cerebronic acid), 2-hydroxytetraeicosenoic acid (alpha hydroxynervonic acid) and 2,4-dihydroxy-3,3-dimethylbutanoic acid (pantoic acid).

5. A composition according to claim 2, wherein said alpha hydroxyacid is an aralkyl or aryl alpha hydroxyacids selected from the group consisting of 2-phenyl 2-hydroxyethanoic acid (mandelic acid); 2,2-diphenyl 2-hydroxyethanoic acid (benzilic acid), 3-phenyl 2-hydroxypropanoic acid (phenyllactic acid), 2-phenyl 2-methyl 2-hydroxyethanoic acid (atrolactic acid) and 4-hydroxymandelic acid.

6. A composition according to claim 2, wherein said alpha hydroxyacid is a polyhydroxy alpha hydroxyacid selected from the group consisting of 2,3-dihydroxypropanoic acid (glyceric acid); 2,3,4-trihydroxybutanoic acid (isomers; erythronic acid, threonic acid); 2,3,4, 5-tetrahydroxypentanoic acid (isomers; ribonic acid, arabinoic acid, xylonic acid, lyxonic acid); 2,3,4,5,6-pentahydroxyhexanoic acid (isomers; allonic acid, altronic acid, gluconic acid, mannoic acid, gulonic acid, idonic acid, galactonic acid, talonic acid); 2,3,4,5,6,7-hexahydroxyheptanoic acid (isomers; glucoheptonic acid, galactoheptonic acid, mannoheptonic acid, etc.).

7. A composition according to claim 2, wherein said alpha hydroxyacid is a polycarboxylic alpha hydroxyacid selected from the group consisting of 2-hydroxypropane-1,3-dioic acid (tartronic acid); 2-hydroxybutane-1,4-dioic acid (malic acid); 2-hydroxy-2-methylbutane-1,4-dioic acid (citramalic acid); 2,3-dihydroxybutane-1,4-dioic acid (tartaric acid); 2,3,4-trihydroxypentane-1,5-dioic acid (isomers; ribaric acid, arabaric acid, xylaric acid, lyxaric acid); 2,3,4,5-tetrahydroxyhexane-, 1,6-dioic acid (isomers; glucaric acid, galactaric acid, mannaric acid, allaric acid, altraric acid, gularic acid, idaric acid, talaric acid); 2-hydroxy-1,2,3-propanetricarboxylic acid (citric acid); 1-hydroxy-1,2,3-propanetricarboxylic acid (isocitric acid); 1-hydroxy-1,2,4-butanetricarboxylic acid (homoisocitric acid); 2-hydroxy-3-hexadecyl-1,2,3-propanetricarboxylic acid (n-hexadecyl citric acid; agaricic acid).

8. A composition according to claim 2, wherein said alpha hydroxyacid is an alpha hydroxyacid selected from the group consisting of glyceruronic acid, erythruronic acid, threuronic acid; 2,3,4-trihydroxypentanuronic acids (isomers; riburonic acid, arabinuronic acid, xyluronic acid, lyxuronic acid); 2,3,4,5-tetrahydroxyhexanuronic acid (isomers; alluronic acid, altruronic acid, glucuronic acid, mannuronic acid, guluronic acid, iduronic acid, galacturonic acid, taluronic acid), and 2,3,4,5,6-pentahydroxyheptanuronic acid (isomers; alloheptanuronic acid, altroheptanuronic acid, glucoheptanuronic acid, mannoheptanuronic acid, guloheptanuronic acid, idoheptanuronic acid, galactoheptanuronic acid, taloheptanuronic acid).

9. A composition according to claim 1, comprising a related acid selected from the group consisting of hydroxyacids.

10. A composition according to claim 9, wherein said hydroxyacid is a beta hydroxyacid.

11. A composition according to claim 10, wherein said beta hydroxyacid is selected from the group consisting of 3-hydroxypropanoic acid (beta-hydroxypropanoic acid), 3-hydroxybutanoic acid (beta-hydroxybutyric acid), 2-phenyl-3-hydroxypropanoic acid (tropic acid); and 3-hydroxy-3,7,11-trimethyldodecanoic acid (trethocanic acid).

12. A composition according to claim 1, wherein said related acid is an alpha ketoacid.

13. A composition according to claim 12, wherein said alpha ketoacid has the generic formula:

$(R_a)COCOOH$ wherein $R_a$ is H, alkyl, aralkyl or aryl group of saturated or unsaturated, isomeric or non-isomeric, straight or branched chain or cyclic form, having 1 to 25 carbon atoms, and in addition $R_a$ may carry F, Cl, Br, I, OH, CHO, COOH and alkoxyl group having 1 to 9 carbon atoms.

14. A composition according to claim 13, wherein said alpha ketoacid is selected from the group consisting of 2-ketoethanoic acid (glyoxylic acid), 2-ketopropanoic acid (pyruvic acid), 2-phenyl-2-ketoethanoic acid (benzoylformic acid), 3-phenyl-2-ketopropanoic acid (phenylpyruvic acid), 2-ketobutanoic acid, 2-ketopentanoic acid, 2-ketohexanoic acid, 2-ketoheptanoic acid, 2-ketooctanoic acid and 2-ketododecanoic acid.

15. A composition according to claim 1, wherein said related acid is a hydroxyacid selected from the group consisting of quinic acid (1,3,4,5-tetrahydroxycyclohexanecarboxylic acid), piscidic acid (4-hydroxybenzyltartaric acid), lactobionic acid (galactopyranosylgluconic acid), ascorbic acid (3-oxo-L-gulofuranolactone), Isoascorbic acid (D-erythro-hex-2-enonic acid r-lactone), 2-hexulosonic acids (isomers; arabino-2-hexulosonic acid, xylo-2-hexulosonic acid, ribo-2-hexulosonic acid, lyxo-2-hexulosonic acid), 5-hexulosonic acids (isomers; arabino-5-hexulosonic acid, xylo-5-hexulosonic acid, ribo-5-hexulosonic acid, lyxo-5-hexulosonic acid).

16. A composition according to claim 1, wherein said related acid is an oligomer of hydroxyacids having the structure:

$(AHA)m-n(H_2O)$ wherein, AHA is a hydroxyacid, m is from 2 to 10, and n=m−1.

17. A composition according to claim 16, wherein:
m is from 2 to 4, and n=m−1, and wherein the AHA in each monomer may be identical or different.

18. A composition according to claim 16, wherein said oligomer is selected from the group consisting of glycolyl glycolate, glycolyl lactate, lactyl lactate, lactyl glycolate, citryl citrate, glycoly citrate, citryl glycolate, lactyl citrate, citryl lactate, malyl malate, malyl glycolate, tartaryl tartrate, tartaryl glycolate, glycolyl tartrate, glycolyl glycoly glycolate and lactyl lactyl lactate.

19. A composition according to claim 1, wherein said alpha hydroxyacid or related acid is the form of an intramolecular lactone.

20. A composition according to claim 19, wherein said intramolecular lactones is selected from the group consisting of gluconolactone, galactonolactone, glucuronolactone, galacturonolactone, gulonolactone, ribonolactone, saccharic acid lactone, pantoyllactone, glucoheptonolactone, mannonolactone, and galactoheptonolactone.

21. A composition according to claim 1, wherein said organic complexing agent has a molecular weight of from about 50 to about 900.

22. A composition according to claim 1, wherein said organic complexing agent has a molecular weight of from about 100 to about 600.

23. A composition according to claim 1, wherein said organic complexing agent is selected from the group consisting of amino acid esters, non-amphoteric amino acid amides, aminosaccharides, aminoalditols and aminocyclitols.

24. A composition according to claim 23, wherein said amino acid ester is selected from the group consisting of alkyl, aralkyl and aryl esters of amino acids.

25. A composition according to claim 24, wherein said amino acid ester is selected from the group consisting of methyl, ethyl, propyl, isopropyl, butyl, pentyl, octyl, lauryl, stearyl, benzyl and phenyl esters of amino acids.

26. A composition according to claim 25, wherein said amino acid portion of the amino acid ester is selected from the group consisting of glycine, alanine, valine, leucine, isoleucine, serine, threonine, tyrosine, cysteine, methionine, aspartic acid, asparagine, glutamic acid, glutamine, arginine, lysine, histidine, phenylalanine, tryptophan, proline, β-alanine, β-aminoisobutanoic acid, homocysteine, homoserine, ornithine and citrulline.

27. A composition according to claim 23, wherein said organic complexing agent is a non-amphoteric amino acid amide.

28. A composition according to claim 27, wherein one or both of the hydrogen atoms of said non-amphoteric amino acid amide are substituted with an alkyl, aralkyl and aryl radical.

29. A composition according to claim 28, wherein said non-amphoteric amino acid amide is selected from the group consisting of glycinmethylamide, glycindimethylamide, glycinamide, alaninamide, valinamide, leucinamide, isoleucinamide, serinamide, threoninamide, tyrosinamide, cysteinamide, methioninamide, asparaginamide, glutaminamide, argininamide, lysinamide, histidinamide, phenylalaninamide, tryptophanamide, prolinamide, β-alaninamide, β-aminoisobutanoic amide, homocysteinamide, homoserinamide, ornithinamide and citrullinamide.

30. A composition according to claim 23, wherein said organic complexing agent is an aminosaccharide that is a derivative or a monosaccharide or oligosaccharide.

31. A composition according to claim 30, wherein said aminosaccharide is selected from the group consisting of erythrosylamines, erythrosamines, threosylamines, threosamines, ribosylamines, ribosamines, arabinosylamines, arabinosamines, xylosylamines, xylosamines, lyxosylamines, lyxosamines, allosylamines, allosamines, altrosylamines, altrosamines, glucosylamines, glucosamines, mannosylamines, mannosamines, gulosylamines, gulosamines, idosylamines, idosamines, galactosylamines, galactosamines, talosylamines, talosamines, glucoheptosylamines, glucoheptosamines, galactoheptosylamines, galactoheptosamines, mannoheptosylamines, mannoheptosamines, octosylamines, octosamines, nonosylamines, nonosamines, tetrulosamines, erythrulosamines, pentulosamines, ribulosamines, arabulosamines, xylulosamines, lyxulosamines, hexulosamines, fructosamines, sorbosamines, tagatosamines, sucrosamines, lactosylamines, lactosamines, trehalosamines, maltosylamines, maltosamines, cellobiosylamines, cellobiosamines, isomaltosylamines, isomaltosamines, gentiobiosylamines, gentiobiosamines, chitobiose and chitobiosylamines.

32. A composition according to claim 23, wherein said organic complexing agent is an aminoalditol.

33. A composition according to claim 32, wherein said aminoalditol is selected from the group consisting of aminoerythritols, aminothreitols, threamine, aminoribitols, ribamine, aminoarabinitols, arabinamine, aminoxylitols, xylamine, aminolyxitols, lyxamine, aminoallitols, allamine, aminoaltritols, altramine, aminoglucitols, glucamine, aminomannitols, mannamine, aminogulitols, gulamine, aminoiditols, idamine, aminogalactitols, galactamine, aminotalitols, talamine, aminoalloheptitols and allohep- tamine.

34. A composition according to claim 23, wherein said organic complexing agent is an aminocyclitol.

35. A composition according to claim 34, wherein said aminocyclitol is selected from the group consisting of cis-aminoinositol, epi-aminoinositols, neo-aminoinositols, myo-aminoinositol, muco-aminoinositols, scyllo-aminoinositols, chiro-aminoinositols, validamine, valienamine and aminopinitols.

36. A composition according to claim 1, wherein said organic complexing agent is present in an amount of from about 0.1 to 50% by weight of the total composition.

37. A composition according to claim 1, wherein said organic complexing agent is present in an amount of from about 1 to 25% by w eight of the total composition.

38. A composition according to claim 1, wherein said alpha hydroxyacid or the related acid is present in an amount of at least about 1% by weight of the total composition.

39. A composition according to claim 1, wherein said alpha hydroxyacid or the related acid is present in an amount of from about 5% to about 10% by weight of the total composition.

40. A composition according to claim 1, wherein said alpha hydroxyacid or the related acid is present in an amount of from 10% to about 20% by weight of the total composition.

41. A composition according to claim 1, wherein said alpha hydroxyacid or the related acid is present in an amount of greater than about 20% by weight of the total composition.

42. A method of treating aging related skin conditions comprising topically applying to the skin, for a period of time and in an amount sufficient to effect changes in the dermis, of a composition according to claim 1.

43. A method according to claim 42, wherein said composition is topically applied to reduce the presence of pigmented and non-pigmented age spots.

44. A method according to claim 42, wherein said composition is topically applied to effect a substantial increase in skin thickness.

45. A method according to claim 42, wherein said composition is topically applied to stimulate synthesis of a dermal component selected from the group consisting of glycosaminoglycans, proteoglycans, collagen and elastic fibers.

46. A method according to claim 42, wherein said alpha hydroxyacid ester is topically applied to effect a detectable decrease in skin lines.

47. A method according to claim 42, wherein said alpha hydroxyacid ester is topically applied to effect a detectable decrease in wrinkles.

48. A method according to claim 42, wherein said alpha hydroxyacid ester is topically applied to photoaged skin.

49. A method according to claim 42, wherein said alpha hydroxyacid acid is topically applied to photodamaged skin.

50. A method according to claim 42, wherein said alpha hydroxyacid acid is topically applied to intrinsically aged skin.

51. A composition according to claim 1, further comprising a cosmetic or topically active agent.

52. A composition according to claim 51, wherein said topically active agent is selected from the group consisting of acyclovir, amphotericins, chlorhexidine, clotrimazole, ketoconazole, econazole, miconazole, metronidazole, minocycline, nystatin, neomycin, kanamycin, phenytoin, octyl dimethyl PABA, octyl methoxycinnamate, PABA and other esters, octyl salicylate, oxybenzone, dioxybenzone, tocopherol, tocopheryl acetate, selenium sulfide, zinc pyrithione, soluble elastin, diphenhydramine, pramoxine, lidocaine, procaine, erythromycin, tetracycline, clindamycin, crotamiton, hydroquinone and its monomethyl and benzyl ethers, naproxen, ibuprof en, cromolyn, retinoic acid, retinol, retinyl palmitate, retinyl acetate, coal tar, griseofulvin, hydrocortisone, hydrocortisone 21-acetate, hydrocortisone 17-valerate, hydrocortisone 17-butyrate, betamethasone valerate, betamethasone dipropionate, triamcinolone acetonide, fluocinonide, clobetasol propionate, minoxidil, dipyridamole, diphenylhydantoin, benzoyl peroxide, 5-fluorouracil, vitamin A acetate (retinyl acetate) and vitamin E acetate (tocopheryl acetate).

53. A method according to claim 42, further comprising the step of topically applying a cosmetic or topically active agent.

54. A method according to claim 51, wherein said topically active agent is selected from the group consisting of acyclovir, amphotericins, chlorhexidine, clotrimazole, ketoconazole, econazole, miconazole, metronidazole, minocycline, nystatin, neomycin, kanamycin, phenytoin, octyl dimethyl PABA, octyl methoxycinnamate, PABA and other esters, octyl salicylate, oxybenzone, dioxybenzone, tocopherol, tocopheryl acetate, selenium sulfide, zinc pyrithione, soluble elastin, diphenhydramine, pramoxine, lidocaine, procaine, erythromycin, tetracycline, clindamycin, crotamiton, hydroquinone and its monomethyl and benzyl ethers, naproxen, ibuprofen, cromolyn, retinoic acid, retinol, retinyl palmitate, retinyl acetate, coal tar, griseofulvin, hydrocortisone, hydrocortisone 21-acetate, hydrocortisone 17-valerate, hydrocortisone 17-butyrate, betamethasone valerate, betamethasone dipropionate, triamcinolone acetonide, fluocinonide, clobetasol propionate, minoxidil, dipyridamole, diphenylhydantoin, benzoyl peroxide, 5-fluorouracil, vitamin A acetate (retinyl acetate) and vitamin E acetate (tocopheryl acetate).

* * * * *